United States Patent [19]

Wittkampf

[11] 4,136,703

[45] Jan. 30, 1979

[54] ATRIAL LEAD AND METHOD OF INSERTING SAME

[75] Inventor: Frederik H. M. Wittkampf, Brummen, Netherlands

[73] Assignee: Vitatron Medical B.V., Dieren, Netherlands

[21] Appl. No.: 884,917

[22] Filed: Mar. 9, 1978

[51] Int. Cl.² ................................................ A61N 1/04
[52] U.S. Cl. .................................................. 128/419 P
[58] Field of Search ...................... 128/404, 418, 419 P

[56] References Cited

U.S. PATENT DOCUMENTS

| | | | |
|---|---|---|---|
| 3,729,008 | 4/1973 | Berkovits | 128/418 |
| 3,865,118 | 2/1975 | Bures | 128/404 |
| 3,902,501 | 9/1975 | Citron et al. | 128/418 |
| 3,949,757 | 4/1976 | Sabel | 128/404 |
| 4,026,303 | 5/1977 | Babotai | 128/418 |
| 4,057,067 | 11/1977 | Lajos | 128/418 |

OTHER PUBLICATIONS

Portsmann et al., "American Journal of Cardiology", vol. 30, Jul. 11, 1972, pp. 74 & 75.

Primary Examiner—William E. Kamm
Attorney, Agent, or Firm—Woodcock, Washburn, Kurtz & Mackiewicz

[57] ABSTRACT

An atrial lead assembly is provided which is adapted for curving into position within the atrium, the lead having a flexible length without any preset curve, and comprising stylet means for introducing a curve into the distal end of the lead. The stylet enables the operator to set the axis of the lead along a curvilinear path adjustable by the operator. The lead has a tip of a continuous helical type adapted to be rotated into contact with the trabeculae, the lead being rotatable about the stylet while the stylet maintains the lead axis in a desired position, whereby the tip is caused to engage the trabeculae. After such engagement, the stylet can be removed, leaving the lead tip in good fixation with the atrial wall.

15 Claims, 8 Drawing Figures

ATRIAL LEAD AND METHOD OF INSERTING SAME

BACKGROUND OF THE INVENTION

1. Field of the Invention

This invention relates to leads, or catheters, adapted for insertion into a patient's heart for transmitting signals between the heart and a device such as a pacer, and more particularly a lead adapted for atrial insertion.

2. Description of the Prior Art

In the field of electronic cardiac pacing, there is a certain utilization of pacers designed to provide stimulus pulses to the patient's atrium or receive signals from the atrium, or both. As with ventricular pacing, it is desirable, if possible, to introduce the catheter or lead transvenously through the superior vena cava. For placement of a lead tip within the ventricle, little difficulty is encountered since the lead can simply be inserted until the tip reaches the apex of the right ventricle. However, the procedure is not quite so simple or so reliable with respect to the atrium, due to the dimensions of the atrium. The atrium has no apex corresponding to the ventricle, and a lead which is simply inserted to the point where the tip is within the atrium would not attain fixation in most cases, since it would be more or less suspended within the atrium. In order to overcome this difficulty, the procedure adopted most generally in the prior art is to introduce a J-shaped or other type of curvilinear electrode which enables the tip to be forced into contact with the inner atrial wall. Examples of such electrodes are seen in many U.S. Pats., including Nos. 3,729,008; 3,865,118; 3,949,757; and 4,057,067.

A common form of atrial lead found in the prior art is a lead having a preset curve at the end of the lead, or the end of the atrial component of the lead in the case of leads designed to have both atrial and ventricular tips. In order to be able to introduce the lead transvenously, the preset curved portion is maintained in a straight form by a stylet while the lead is being introduced into the patient's body. Upon having positioned the lead within the atrium, the stylet is withdrawn, permitting the atrial tip to assume the preset curvilinear form. However, with such a lead the physician who is introducing the lead has relatively little capability for positioning the tip after the stylet has been withdrawn. Rotation of the lead about its axis causes the entire curvilinear tip portion to rotate or flop around relative to the lead axis just preceding the curved portion; it is not possible, with this type of lead, to simply rotate the distal end where the electrode tip is located while holding the axial configuration fixed.

In the U.S. Pat. to Babotai, No. 4,026,303, issued May 31, 1977 and assigned to the same assignee as this application, there is disclosed an endocardial electrode having a closed helical tip which is particularly well adapted for engaging the trabeculae on the inner lining of the heart wall. This type of tip is adaptable for use in an atrial lead as well as a ventricular lead. In utilizing the electrode as shown in the Babotai patent, it is necessary for the physician to rotate the proximal end of the electrode, thereby imparting rotation to the distal tip, the rotation enabling the proper positioning of the tip so that the trabeculae can enter and engage the open grooves of the closed helix. However, this sort of closed helical tip can not be utilized with the prior art type of atrial lead since rotation of the proximal end of the lead would cause the entire curvilinear portion at the distal end to flop around, such that the helical tip could not be rotated into fixation with the trabeculae. There is thus a need for a lead assembly which enables the physician to insert the lead transvenously until the atrial tip portion has reached the atrium, to then introduce a curvilinear form to the atrial tip so that it comes into engagement with the atrial wall, and to then rotate the atrial tip about its axis while such axis is maintained substantially fixed, so that the tip can be brought into optimal engagement and fixation with the atrial trabeculae.

SUMMARY OF THE INVENTION

It is a primary object of the invention to provide a lead adaptable for easy and reliable insertion into the atrium, which lead enables the operating physician to obtain good penetration of the lead tip within the atrial trabeculae.

It is another object of this invention to provide an atrial lead which overcomes the disadvantages of the prior art, in that the distal end portion can be caused to assume a curvilinear form and the distal tip of said lead may be rotated about its axis while such axis is maintained substantially fixed.

It is another object of this invention to provide a transvenous atrial lead adapted for accomplishing good fixation between the electrode tip of the lead and the atrial wall, the lead possessing improved characteristics over the prior art in terms of being able to position the lead within the atrium and also rotate the atrial lead tip while maintaining such position.

In accordance with the above objects, there is provided a lead particularly adapted for placement in a patient's atrium, the lead having a conventional encased conductor portion running substantially the length of the lead to an atrial tip fixed thereto and including an electrical conductor for conducting signals between said atrial tip and the proximal end, in combination with a stylet adapted for insertion within the lumen of the encased conductor, which stylet when inserted causes the axis of the atrial end of the lead to assume a curvilinear form. The atrial tip preferably has a closed helical configuration adapted for rotation for engagement of the trabeculae on the atrial wall. The conductor portion is rotatable about the stylet, so that the operating physician introduces the stylet to the point where the atrial tip assumes a desired curvilinear form and then restrains the stylet from rotational movement while rotating the proximal end of the conductor, thereby imparting desired rotation to the helical tip to achieve engagement of the tip to the atrial trabeculae.

DESCRIPTION OF THE PREFERRED EMBODIMENTS

In the description of the lead assembly of this invention, the term lead is used synonomously with the term "catheter" as that term is frequently used in the pacing art. The term "electrode" is likewise used in the art to denote the entire apparatus, but in this application electrode denotes simply the contact portion of the lead through which signals are delivered directly to the body wall, or are sensed. The lead is employed for delivering electrical signals, such as pacing stimulus signals produced by a cardiac pacer, to a point in a patient's body, and/or sensing signals from such point in the patient's body and delivering the sensed signals to the pacer or other device. The lead of this invention will be particularly illustrated as an atrial lead, but it is noted at the start that the lead may be adapted as an atrioventricular lead for transmitting signals between a pacer and both the atrium and the ventricle.

Figure 1A:
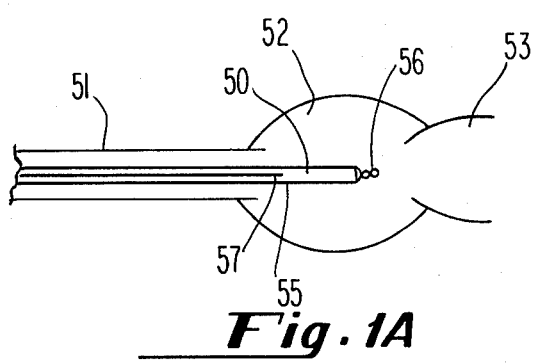
FIG. 1A is a schematic representation of the lead of this invention with its distal tip introduced into the atrium, but before the stylet has been introduced to the point of imparting a curve to the distal end portion of the lead.
Figure 1B:
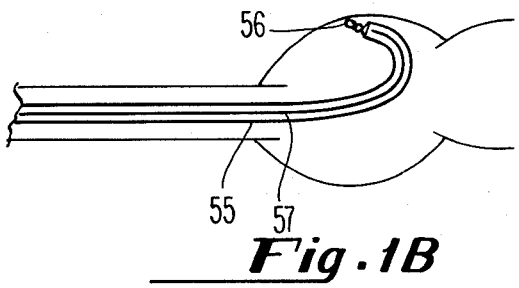
FIG. 1B is a schematic representation of the lead of FIG. 1A, with the stylet introduced to the point of imparting a curvilinear form to the distal end portion of the lead.

Referring first to FIGS. 1A and 1B, there is shown in diagrammatic form the basic concept of the lead of this invention for providing a desired curve to the distal tip of the lead (or to the distal tip of the atrial component in the case of an atrioventricular lead). In FIG. 1A, the lead 55 is shown positioned with its distal tip 56 within the patient's atrium 52, access having been obtained through the superior vena cava 51. The lead 55 has conventional characteristics for such leads, in that it is sufficiently flexible so that it can be inserted transvenously, is encased with a suitable watertight and biocompatible material, and carries at least one electrical conductor for transmitting signals between the distal tip and the proximal end which is connected to a pacer or other like device. The lead may be positioned with the distal tip short of the ventricle 53 and still within the atrium, by conventional methods used in the art. The lead comprises a stylet 57 which is here illustrated by simply a continuous line, which stylet is inserted with its distal tip short of the distal end of the lead. In other words, the stylet is not inserted all the way as far as it can be inserted, with the consequence that the flexible catheter 55 does not assume any predetermined curvilinear form. In FIG. 1B, the same lead assembly is illustrated with the stylet 57 advanced until the tip is substantially at the distal end of the lead 55, thereby introducing to the distal portion of the lead a curvilinear form similar to the preset form of the stylet wire. This sequence as shown in FIGS. 1A and 1B is the reverse of the typical prior art arrangement wherein the stylet is initially fully inserted to maintain the lead in a straight form, and then the stylet is removed so that the lead assumes a preset curvilinear form. In applicant's invention, the tip 56 is first fixed to the atrial wall, to hold it in position, before the stylet is removed. Of course, if such fixation is not good, then when the stylet is removed the lead tip resumes the form as shown in FIG. 1A. Accordingly, it is necessary to have a lead tip 56 which is capable of providing secure fixation to the inside of the atrium, and means for manipulating the lead assembly so as to accomplish such good fixation. The desired tip 56 is provided in accordance with the disclosure of the aforementioned U.S. Pat. No. 4,026,303, which is incorporated by reference. That patent shows a closed helical tip, marketed under the name HELIFIX, which when placed in the trabeculae and rotated accomplishes a good engagement within such trabeculae, providing excellent fixation. As disclosed in the issued patent, the electrode tip is closed, or rounded so that the tip engages but does not enter the trabeculae. The open grooves of the closed helical tip are dimensioned to provide optimum opportunity for the trabeculae to become entwined therein, thereby achieving good fixation.

Figure 2A:
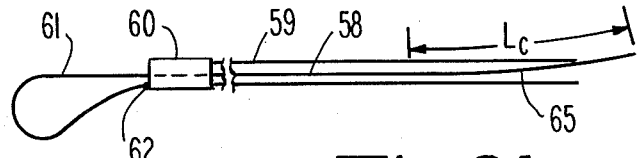
FIG. 2A is a schematic representation of the stylet which is used as part of the lead assembly of this invention, illustrating the condition where most of the stylet wire which carries a resilient preset curve is within the restraining stylet tube.
Figure 2B:
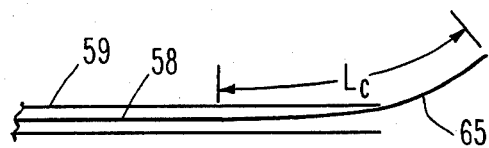
FIG. 2B shows a schematic representation wherein about half of the preset curve of the stylet wire has been moved forward and outside of the stylet restraining tube.
Figure 2C:
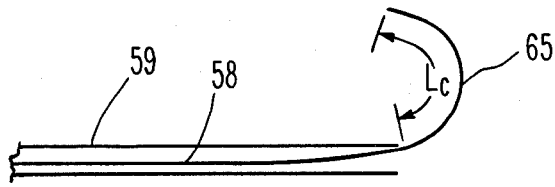
FIG. 2C is a schematic representation showing the stylet in a position where all of the portion of the stylet wire which carries the preset curve is free from the restraint of the stylet restraining tube.

As is also disclosed in the aforementioned U.S. Pat. No. 4,026,303, the length of the lead proximal to the closed helical tip is hollow to permit insertion of a stylet, for rotating the electrode around the stylet and positioning the tip for optimum contact for stimulation. In the case of placement in the ventricle, the stylet is simply inserted the full length of the lead lumen, and then the lead is rotated around the stylet. However, for the atrial application, since the distal end of the stylet carries a resilient preset curve, this curve is introduced at the end of the lead lumen only after positioning of the atrial tip within the atrium. The technique for doing this is illustrated in FIGS. 2A–2C. In FIG. 2A, the stylet is shown as comprising a wire 58 having a distal portion 65 with a length Lc which carries a resilient preformed curve. Wire 58 is suitably made of steel, such that the portion 65 always maintains its curve when free from restraint. Wire 58 is positioned axially through a containing flexible metal tube 59 of sufficient strangth to restrain tip portion 65 from assuming its preset form as long as such portion is within tube 59. As seen in FIGS. 2B and 2C, as the distal portion 65 is pushed out of the restraining tube 59, the freed end assumes the preset curvilinear form. The curvilinear form of portion 65 may have a curvature of up to 180°, or more, the operating physician being able to utilize any portion of such curve by adjusting the length of the portion 65 which extends outward from the distal end of tube 59.

As seen in FIG. 2A, at the proximal end of the stylet there is provided a knob or housing 60 through which the wire 58 is threaded and looped at extension 61. The proximal end of the wire is connected, as by soldering, to the knob at point 62. The operating physician may adjust the length by which portion 65 extends from tube 59 by holding knob 60 with one hand and moving the extension portion 61 into or out of the knob. In practice, prior to inserting the lead 55 into the patient's vein, the stylet is positioned at about the position shown in FIG. 2A and inserted into the lumen 50. Since none or very little of the preset curved portion 65 extends from the restraining tube 59, the lead has a normal flexible property which is required for inserting it through the vein. After it has been determined that the tip 56 is located within the atrium, then the physician adjusts the position of portion 65 by manipulation of extension portion 61, until he determines that the lead tip has assumed a desired curvilinear form so that the tip 56 has come into contact with the trabeculae.

Figure 3:
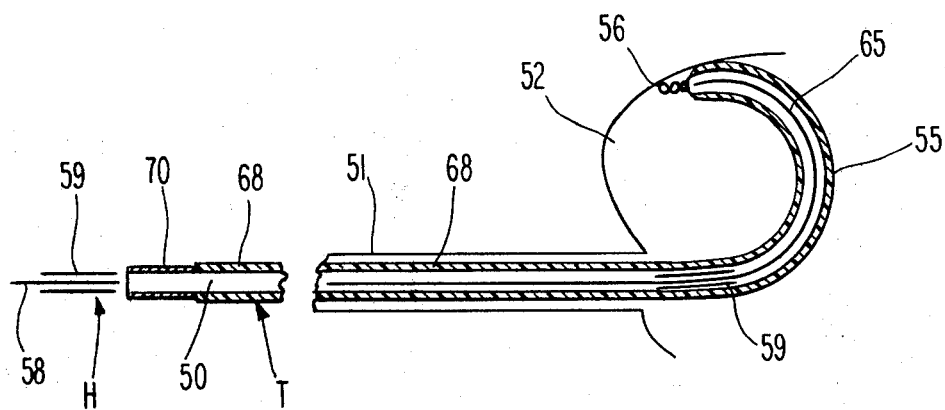
FIG. 3 is an enlarged schematic representation showing the lead, with stylet fully extended and in position within an atrium, and illustrating how the lead is manipulated to obtain optimal fixation of the lead tip within the atrium.

Referring to FIG. 3, there is shown an enlarged diagram of the lead assembly of this invention, with the stylet extended so as to cause the distal end portion of the lead to assume a curvilinear form, carrying helical end 56 into contact with the atrial wall. The end portion 65 is shown extended from the restraining tube 59 so that its preset curve causes the lead 55 to curve around in a J form, so that the distal tip 56 is pressed against the atrial wall. In this position, tip 56 is ready to be rotated so as to make engaging contact with the atrial trabeculae. The physician holds the stylet tubing 59, as indicated by the designation H, with one hand, and turns the lead with the other hand at a proximal point such as indicated by the designation T, thereby causing the lead to rotate about the stylet. Since the stylet does not rotate, the axis of the lead is maintained in position while the helical tip 56 rotates. The physician may, as desired, urge the entire lead assembly forward at the same time that the lead is rotated, to enhance fixation of the helical tip around and within the trabeculae. Note also, as indicated in FIG. 3, that a proximal connecting portion 70 is provided for connection to a pacer or the like, the stylet being suitably introduced through the axial opening in the end of the connector portion 70 into and through the length of the lumen 50.

Figure 4A:
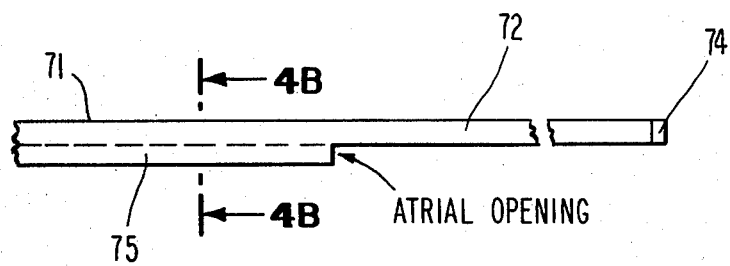
FIG. 4A is a schematic side view of a portion of a lead assembly adapted for supplying both an atrial electrode and a ventricular electrode.
Figure 4B:
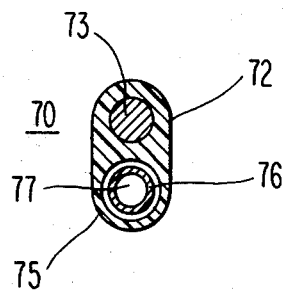
FIG. 4B is a cross sectional view of FIG. 4A taken along the line 4B–4B.

Referring now to FIGS. 4A and 4B, there is shown an illustration of an embodiment of the lead assembly of this invention whereby it is adapted to be an atrioventricular lead supplying an atrial electrode and a ventricular electrode. As seen in FIG. 4A, the main length 71 of the lead assembly 80 has a ventricular portion 72 and an atrial portion 75. The ventricular portion 72 carries a conductor element, suitably in helical form, throughout its length and connects to a ventricular electrode 74, for delivering signals to the ventricle and, as in a demand pacer, also for sensing natural heartbeats at the ventricle. Portion 72 is conventional, and the details of construction are well known in the prior art. Portion 75, as seen in cross-sectional view 4B, contains an open tube into which the atrial lead 76 of this invention may be inserted. Atrial lead 76 comprises an axial lumen 77, providing for insertion of a stylet as in the preferred embodiment of this invention. Upon positioning the entire assembly 80 transvenously to the point where the ventricular tip is at the apex of the ventricle, the atrial lead component 76 is pushed through portion 75 until it comes out of the atrial opening, whereby the physician positions the atrial tip as hereinbefore discussed. By this manner, there is also provided an atrioventricular embodiment of the invention.

I claim:

1. A lead particularly adapted for placement in a patient's atrium, comprising:
    an encased conductor portion running substantially the length of said lead and containing a lumen along the axis thereof, having an electrical conductor for conducting signals between a first proximal end of said lead and the distal end;
    an electrode in fixed mechanical and electrical contact with said electrical conductor at said distal end of said lead adapted for delivering signals to and sensing signals from said atrium;
    stylet means adapted for insertion within said lumen and for cooperation with said encased conductor portion for causing the axis of said conductor portion to take a curvilinear form at the distal end of said conductor portion; and
    said stylet means comprising an element with a preset curve portion and means for introducing into said conductor distal portion a portion of said preset curve portion and for restraining the remainder of said preset curve portion from assuming its preset form, whereby said conductor distal portion maintains only the curve of said introduced portion.

2. The lead as described in claim 1, wherein said preset curve portion comprises a curve of about 180°, and said introducing means enables maintaining said conductor curve at a curve within the range of 0° to about 180°.

3. The lead as described in claim 1, wherein said conductor portion is rotatable with respect to said stylet means, whereby said electrode is rotatable about a fixed curvilinear axis.

4. The lead as described in claim 1, wherein said electrode has a closed helical configuration.

5. The lead as described in claim 1, wherein said stylet means comprises a wire having said preset curve portion at its distal end, a hollow tube adapted to contain a portion of said wire within its hollow interior, and wherein said introducing means permits extension of a portion of said preset curve portion out of the distal end of said tube.

6. An intravascular type lead for use with a pacer, having a first end adapted for connection to said pacer and a second end having at least one electrode, comprising a flexible casing containing an electrical conductor extending substantially the length of said lead, said conductor electrically connecting said first and second ends, said casing having an axial lumen extending substantially along its axis; and stylet means insertable into said lumen for maintaining a portion of said lead at said second end with a curvilinear axis, said stylet means comprising a resilient member having at least a portion which normally assumes a predetermined curvilinear form, and restraining means for restraining said resilient member from assuming said normal form, whereby said electrode is positionable at a first position.

7. The lead as described in claim 6 said resilient member being moveable relative to said restraining member so that a part of said portion may be released from being restrained by said restraining means.

8. The lead as described in claim 6, in integral combination with a second encased conductor for delivering signals between said pacer and a second position.

9. A flexible lead without preset form for use in connection with an electronic pacer and being adapted to receive a stylet, in combination with a stylet having an end portion preconditioned to assume a curvilinear form, said stylet being positionable in said lead with said end portion at about the distal end of said lead, whereby said lead distal end is caused to assume said curvilinear form, said lead having an axial lumen within which said stylet is positioned, said stylet having a first element with an end portion preconditioned to assume a curvilinear form and a second element surrounding at least a portion of said first element, whereby said lead is rotatable about said stylet while said stylet holds the lead axis substantially fixed.

10. A method of positioning the distal end of a flexible lead in a predetermined portion of a human body, utilizing a lead adapted to axially receive a stylet having a resilient preconditioned curve portion, comprising performing the steps of:

holding at least a portion of said curve portion from assuming its preconditioned form;

inserting said stylet part way into said lead and positioning said lead into the human body so that said lead distal end is about at said predetermined portion and with a first normal form;

then moving said stylet so that at least a part of said curve portion moves into said lead distal end and is released to assume said curvilinear form, whereby said lead distal end assumes at least part of the form of said curve;

and then rotating said lead about said stylet, whereby the distal end of said lead rotates about its axis.

11. The method as described in claim 10, comprising restraining said stylet from rotation about its axis while rotating said lead about said stylet, whereby said lead rotation does not cause movement of said lead axis.

12. The method as described in claim 10, wherein the step of then moving comprises moving only part of said curve portion into said lead distal end so that said lead distal end assumes only a portion of said curve.

13. The method as described in claim 10, wherein the step of then moving comprises moving the stylet so that said lead distal end assumes substantially all of said curve.

14. The method as described in claim 11, comprising moving said lead along its axis while rotating it about its axis.

15. A lead system comprising:
a. a flexible lead having an axial lumen, a conductor extending substantially the length of said lead, and an electrode at about the distal tip of said lead and electrically connected to said conductor; and
b. a stylet positioned within said lumen, said stylet having a flexible element with an end length having a preset curvilinear form, means positioned proximal from the distal end of said stylet for restraining said end length from taking said preset form, said flexible element being movable relative to said restraining means such that when it is moved toward said distal tip said end length is free to take said preset form and cause the distal end portion of said lead to take said preset form.

* * * * *